US006871446B1

(12) United States Patent
Yamashita

(10) Patent No.: US 6,871,446 B1
(45) Date of Patent: Mar. 29, 2005

(54) MICROBIAL BLEND COMPOSITIONS AND METHODS FOR THEIR USE

(76) Inventor: Thomas T. Yamashita, 677 E. Olive, Turlock, CA (US) 95380

( * ) Notice: Subject to any disclaimer, the term of this patent is extended or adjusted under 35 U.S.C. 154(b) by 0 days.

(21) Appl. No.: 09/695,531

(22) Filed: Oct. 23, 2000

(51) Int. Cl.[7] .................................................. C05F 11/08

(52) U.S. Cl. .............................. 47/58.1 SC; 47/58.1 R; 438/252.4; 438/252.5

(58) Field of Search ....................... 47/58.1 R, 58.1 SC, 47/1.01 R; 435/252.4, 252.5

(56) References Cited

U.S. PATENT DOCUMENTS

| | | | | | |
|---|---|---|---|---|---|
| 4,077,793 | A | * | 3/1978 | Krupicka | 71/7 |
| 4,642,131 | A | * | 2/1987 | Hoitink | 435/253 X |
| 4,952,229 | A | * | 8/1990 | Muir | 71/7 |
| 5,378,460 | A | * | 1/1995 | Zuckerman et al. | 424/93.461 |
| 5,549,729 | A | | 8/1996 | Yamashita | |
| 5,582,627 | A | | 12/1996 | Yamashita | |
| 5,660,612 | A | * | 8/1997 | Bernier et al. | 71/15 |
| 5,695,541 | A | * | 12/1997 | Kosanke et al. | 71/7 |
| 5,696,094 | A | | 12/1997 | Yamashita | |
| 5,797,976 | A | | 8/1998 | Yamashita | |
| 5,939,086 | A | * | 8/1999 | Levy | 424/405 |
| 6,194,193 | B1 | * | 2/2001 | Drahos et al. | 47/58.1 X |

FOREIGN PATENT DOCUMENTS

| | | | | | |
|---|---|---|---|---|---|
| EP | 0223661 A1 | * | 5/1987 | | |
| FR | 2806420 A1 | * | 9/2001 | | |
| JP | 06157226 A | * | 6/1994 | | A01N/63/00 |
| WO | WO 97/31879 | * | 9/1997 | | |
| WO | WO 00/13502 | | 3/2000 | | |
| WO | WO 00-38513 | | 7/2000 | | |
| WO | WO 02/46126 A1 | * | 6/2002 | | C05F/3/04 |

OTHER PUBLICATIONS

APS Press, "Mycorrhizae and Plant Health", (1994), pp. 1–45.

Atlas and Bartha, Microbial Ecology: Fundamentals and Applications, Second Edition., "Interactions among Microbial Populations", (1987), pp. 101–166.

* cited by examiner

*Primary Examiner*—Jeffrey L. Gellner
(74) *Attorney, Agent, or Firm*—Bret E. Field; Bozicevic, Field & Francis LLP

(57) ABSTRACT

Microbial blend compositions and method for their use are provided. The subject compositions comprise a plurality of distinct microbial species that all share the following characteristics: (i) are antagonistic against a plurality of microbial pathogens; (ii) are non-pathogenic towards plants and animals; (iii) are tolerant of high temperatures; (iv) grow rapidly; and (v) proliferate on a complex substrate. In many embodiments, the compositions further include a carrier, e.g., a liquid or solid carrier medium. In practicing the subject methods, the compositions are applied to at least one of soil and plant tissue, and in certain embodiments are applied in conjunction with a complex substrate. Also provided are methods of preparing the subject compositions.

17 Claims, No Drawings

MICROBIAL BLEND COMPOSITIONS AND METHODS FOR THEIR USE

FIELD OF THE INVENTION

The field of this invention is agriculture.

BACKGROUND OF THE INVENTION

Agriculture is the science, art, and business of cultivating the soil, producing crops, raising livestock; and farming. With respect to cultivating the soil and producing crops, it is well known to add various fertilizing and other compositions to the soil and/or plant foliage in order to improve results. Agents that have been added to soil and/or plant tissues include microbial agents, which impart some beneficial property to the soil and/or plant to provided for desirable results.

There is continued interest in the development of new microbial formulations that are capable of providing beneficial results in agriculture and related fields.

Relevant Literature

U.S. Pat. Nos. of interest include: 5,797,976; 5,696,094; 5,582,627; and 5,549,729. PCT applications of interest include: WO 00/13502 and WO 00/38513. See also: Mycorrhizae and Plant Health, F. L. Pfleger & R. G. Linderman, eds (1994) pp. 1–45; The Nature and Practice of Biological Control of Plant Pathogens, R. J. Cook & K. F. Baker (1983); and Microbial Ecology, Fundamentals and Applications. R. M. Atlas & R. Bartha, pp. 99–106.

SUMMARY OF THE INVENTION

Microbial blend compositions and methods for their use are provided. The subject compositions are made up of a plurality of distinct microbial species that all share the following characteristics: (i) are antagonistic against a plurality of microbial pathogens; (ii) are non-pathogenic towards plants and animals; (iii) grow rapidly; (iv) are tolerant of high temperatures; and (iv) readily proliferate on a complex substrate. In many embodiments, the compositions further include a carrier, e.g., a liquid or solid carrier medium. In using the subject compositions, the compositions are applied to at least one of the soil and plant tissue, and in certain embodiments are applied in conjunction with a complex substrate. Also provided are methods of preparing the subject compositions.

DESCRIPTION OF THE SPECIFIC EMBODIMENTS

Microbial blend compositions and methods for their use are provided. The subject compositions are made up of a plurality of distinct microbial species that all share the following characteristics: (i) are antagonistic against a plurality of microbial pathogens; (ii) are non-pathogenic towards plants and animals; (iii) grow rapidly; (iv) are tolerant of high temperatures; and (v) readily proliferate on a complex substrate. In many embodiments, the compositions further include a carrier, e.g., a liquid or solid carrier medium. In practicing the subject methods, the compositions are applied to at least one of the soil and plant tissue, and in certain embodiments are applied in conjunction with a complex substrate. Also provided are methods of preparing the subject compositions.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

Microbial Blend Compositions

As summarized above, the subject invention provides a composition that is made up of a plurality of distinct microbial species. By plurality is meant at least 2, and usually at least 5, where in many embodiments the number of different microbial species in the compositions may be as high as 10, 15 or higher. A feature of the subject compositions is that each of the constituent members of the plurality of microbial species has the following characteristics: (a) is antagonistic against a plurality of microbial pathogens; (b) is non-pathogenic towards plants and animals; (c) is tolerant of high temperatures; (d) grows rapidly; and (e) readily proliferates on a complex substrate. Each of these characteristics is now described in greater detail below.

By antagonistic against a plurality of microbial pathogens is meant that microbial species inhibits the growth of a plurality of known pathogenic microbial species, e.g., as determined in the assay described in the Experimental Section, infra. By plurality is meant at least 2, usually at least 5 and more usually at least 10. Specific known pathogenic microbial species against which the microbial species of the subject compositions preferably show antagonism include, but are not limited to:

(1) *Verticillium dahliae* (7) *Monilochaetes infuscans*
(2) *Fusarium solani* (8) *Rhizoctonia solani*
(3) *Cylindrocarpon obtusisporum* (9) *Sclerotinia scierotiorum*
(4) *Pythium aphanidermatum* (10) *Sclerotinia minor*
(5) *Phytophthora megasperma* (11) *Sclerotium rolfsii*
(6) *Phymatotrichum omnivorum* (12) *Botrytis cinerea*

In certain preferred embodiments, the microbial species of the subject compositions show antagonism against at least 5 of the above pathogens, and more preferably against 10 of the above pathogens, and most preferably against all of the above pathogens. A particular microbial species is considered to antagonistic against a microbial pathogen if it shows positive results in the assay described in greater detail in the Experimental Section, infra.

The microbial species of the subject compositions must also be non-pathogenic or non-toxic with respect to an array of plants and animals. Plants against which the microbial species of the subject compositions show substantially no or no toxicity include: Tomato Seedlings, Pepper Seedlings, Cucumber Seedlings, Radish Seedlings, and Grapevine Seedlings. Toxicity against these plants may be assessed using the assay described in the Experimental Section, infra. Animal species against which the particular microbial species of the subject compositions show substantially no or no toxicity as determined using the assay described in the experimental section, supra, include: mice and rabbits.

The microbial species of the subject compositions (microbial blends) must also be tolerant of high temperatures. By tolerant is meant that they are not inactivated or killed by exposure to high temperatures. As such, they are not inactivated or killed when exposed to temperatures up to 100, usually up to 120 and more usually up to 140° F. or higher.

In addition, microbial species of the subject compositions are rapid growers, i.e., they rapidly proliferate as determined using the assay described in the Experimental Section, infra. Using this growth assay, a species must meet or exceed 1 cm beyond the circle edge within twenty four hours to be a species suitable for inclusion in the subject compositions.

Additional preferred characteristics in many embodiments include tolerance to a wide range of pH conditions. As such, the species members of the subject compositions are preferably tolerant of pH conditions that range from 3.0 to 8.0. In addition, species present in the subject compositions preferably retain viability following a minimum of at least 100 days and usually at least 120 days in liquid suspension maintained at 70° F.

In addition to the above parameters, microbial species of the subject invention are those that provide for desired results in the greenhouse assays described in the experimental section, infra. In these assays, parameters that are evaluated are germination and stand %, completion of stand to production and/or harvest, production and quality, and post germination and post-stand infection.

In addition to the above requirements, all of the constituent members of the subject microbial blend compositions are ones that rapidly proliferate on a complex substrate. By complex substrate is meant a nutrient composition of matter that includes varied chain carbohydrates, amino acids, proteins, alcohols, organic acids, phenol derivatives and various cofactors. A representative complex substrate is provided in the experimental section, infra. Furthermore, complex substrates are disclosed in U.S. Pat. Nos. 5,797,976; 5,696,094; 5,582,627; and 5,549,729; and published PCT application Nos. WO 00/13502 and WO 00/38513, the disclosures of which are herein incorporated by reference. A given microbial species is one that rapidly grows on a complex substrate if it grows on the substrate at a rate that is at least about 2 fold, usually at least about 5 fold and more usually at least about 10 fold faster than the specific pathogenic species disclosed above.

In certain embodiments, the constituent members of the subject microbial blend compositions are those that have been cultured or proliferated on a complex substrate, as described above and further detailed in the Experimental Section, infra.

The subject microbial blend compositions are further characterized in that they generally include at least 1 bacterial species and at least 1 fungal species. In many embodiments, the number of bacterial species in the composition is at least 5, while the number of fungal species is at least 2. In certain embodiments, the microbial species are naturally occurring species which are not genetically modified, i.e., have not been manipulated through recombinant DNA technology. Specific bacterial species of interest include, but are not limited to: *Bacillus subtilis; Bacillus thuringiensis; Bacillus cereus; Bacillus megaterium; Bacillus penetrans; Arthrobacter paraffineus*; and *Pseudomonas fluorescens*. Specific fungal species of interest include, but are not limited to: *Trichoderma viride, Trichoderma harzianum, Trichoderma polysporum, Trichoderma hamatum, Trichoderma koningii, Gliocladium virens, Gieocladium roseum, Gliocladium catenulatum, Penicillium oxalicum, Penicillium lilacinum, Penicillium nigricans, Penicillium chrysogenum, Penicillium frequentens*, and the like.

Preferably, the subject compositions are substantially, if not entirely, free of microbial species that do not meet the above described parameters. By substantially, free is meant that less than 1%, usually less that 0.5% and more usually less than 0.1% of the total number of microbial species in the composition do not meet the above described parameters.

The subject microbial blend compositions may include a carrier medium, which carrier medium may be a liquid or solid. Liquid carrier mediums of interest include aqueous mediums, e.g., water, which may or may not include additional components, e.g., which may or may not include additional components, e.g., glycerin, alcohol(s), polymers, organic acid(s), microbial by-products such as amino acids, various organic acids, complex carbohydrates, macronutrients, micronutrients, vitamins & cofactors, sterols, proteins, gums (e.g. guar gum, xanthan gum), liquid fertilizers, liquid substrates, e.g., as found in co-pending patent application serial no. 9/222,459; and the like. When present in a liquid medium, the total number of microbial species in the medium is generally at least about $1\times10^5$ cfu/ml, usually at least about $1\times10^9$ cfu/ml and more usually at least about $1\times10^{12}$ cfu/ml. Carrier materials of interest also include solid media, e.g., inactivated seed, viable seed, prilled fertilizer, pelletted fertilizer, potting soil, compost, soybean or related meal, greenwaste and related organic waste, manure, fruit culls, talcum, dry mineral preparations, etc. and the like. When combined with a solid medium, the total number of microbial species in the overall composition generally ranges from about $1\times10^3$ to $1\times10^{14}$, usually from about $1\times10^4$ to $1\times10^{12}$ and more usually from about $1\times10^5$ to $1\times10^9$.

Methods of Use

In practicing the subject methods, the subject compositions are applied to at: least one of: the plant, a portion thereof and soil associated therewith. As such, the composition is, in many embodiments, applied to foliage of the plant, e.g. either the entire part of the plant which is above the soil level or a portion thereof, e.g. fruit, leaves, etc. In other embodiments, the composition is applied to soil associated with the plant, i.e. soil proximal to the plant in which the plant is growing, i.e. soil that is contacted by the roots of the plant or from which the plant's roots ultimately obtain nutrients and/or water.

A variety of different application protocols may be employed to apply the subject compositions, where the particular protocol employed depends, at least in part, on whether the particular compositions is a solid or liquid composition. Where the compositions is a liquid, in certain embodiments, the liquid composition is contacted with the soil. By contact is meant that the composition is introduced into the soil. As such, contact can include spraying so that the composition soaks into the soil, injecting the composition into the soil, flooding the soil with the composition, and the like. In yet other embodiments, the composition is contacted with at least a portion of the foliage of the plant. By contact in this context is meant that the composition is placed on the surface of the foliage of the plant(s) to be treated, where the term "foliage" is used broadly to encompass not only the leaves of the plant, but every other part of the plant that is not underground, i.e., below the soil surface, such that the term "foliage" includes leaves, stems, flowers, fruit, etc. Contact may be by any convenient method, including spraying, applying etc.

Depending on the particular protocol being performed and the desired outcome, as well as the nature of the composition, the environmental conditions and any other factors, the composition may be applied more than once over a given period of time. As such, the composition may be applied daily, weekly, every two weeks, monthly etc.

In many embodiments of the subject invention, the liquid compositions described above are applied or delivered in combination with an aqueous delivery vehicle. The aqueous delivery vehicle may be pure water, e.g. tap water, or an aqueous compositions that includes a carbohydrate source and other components. Of interest in many embodiments as aqueous delivery vehicles are those aqueous compositions described in copending application Ser. Nos. 09/149,930 and 09/222,459, as well as those described in U.S. Pat. Nos. 5,797,976; 5,696,094; 5,582,627; and 5,549,729; and published PCT application Nos. WO 00/13502 and WO 00/38513, the disclosures of which are herein incorporated by reference (and specifically, the complex substrates disclosed in these patents, applications and publications); the disclosures of which are herein incorporated by reference. When delivered in combination of with an aqueous delivery vehicle, the ratio of the liquid microbial blend composition to vehicle typically ranges from about 4 oz microbes with 27,000 gal vehicle to 10 gal microbes with 27,000 gal vehicle, usually from about 1 qt microbes with 27,000 gal vehicle to 5 gal microbes with 27,000 gal vehicle and more usually from about 2 qt microbes with 27,000 gal vehicle to 2.5 gal microbes with 27,000 gal vehicle.

The rate at which the subject liquid compositions are applied to the plants may vary depending on the particular nature of the composition and the method by which it is applied, so long as a sufficient amount of the composition is applied to obtain the desired results. In many embodiments where the liquid compositions are applied to the soil, the rate of application ranges from about 4 oz to 5 gal, usually from about 1 qt to 2.5 gal and more usually from about 2 qt to 1 gal/acre. Alternatively, where the liquid compositions are applied to plant tissue, e.g., foliage, they are generally applied at a rate of about 4 oz to 10 gal, usually from about 1 qt to 5 gal and more usually from about 2 qt to 2.5 gal liquid composition per 100 gallons liquid carrier, e.g., water with which the composition is blended immediately prior to application.

In those embodiments where the composition is a dry composition, e.g., a blend coated onto a dry carrier, such as inactivated seed, etc., the composition is, in many embodiments, applied to the soil. Application may take various formats, including broadcast onto the soil top, e.g., 4 to 10 inches, or to the soil surface. The dry composition may also be blended with seeded species during drilling. Other applications protocols may be employed, as are convenient. In many embodiments of using the dry compositions, the compositions are applied at a rate of 8 oz to 500 lbs, usually from about 2 lbs to 40 lbs and more usually from about 15 lbs to 200 lbs/acre.

Utility

The subject methods and compositions find use in a variety of different applications. For example, the subject compositions and methods may be used for: 1) Antagonism of soil-borne pathogens, e.g., as evidenced by a 10%–100% reduction in inoculum levels as compared to a control; 2) Antagonism of soil-overwintering pathogens, e.g. as evidenced by a 10%–100% reduction as compared to a control; 3) Increased release of tied-up minerals, as evidenced by a 25%–500% increase as compared to a control; 4) Antagonism of pests and nematodes, as evidenced by a 10%–100% reduction as compared to a control; 5) Increased water infiltration rates as evidenced by a 25%–800% increase as compared to a control; 6) Increased water-holding capacity of soil as evidenced by a 5%–50% increase as compared to a control; 7) Aerial pathogen antagonism, as evidenced by a 10%–100% reduction as compared to a control; 8) Aerial pest antagonism, as evidenced by a 10%–100% reduction as compared to a control; 9) Reduced freeze hypersensitivity, as evidenced by a 10%–100% reduction as compared to a control; 10) Extended shelf life of fruits & vegetables as evidenced by a 10%–100% increase as compared to a control; 11) Antagonism of insect pests as evidenced by a 10%–100% reduction as compared to a control; 12) Antagonism of soil-borne pathogens as evidenced by a 10%–100% reduction as compared to a control; 13) Antagonism of soil-overwintering pathogens as evidenced by a 10%–100% reduction as compared to control; 14) Increased release of tied-up minerals as evidenced by a 10%–100% increase as compared to a control; 15) Antagonism of nematode pests as evidenced by a 10/o 100% reduction as compared to a control; etc.

Methods of Making

Also provided are methods of making the subject formulations. A representative manufacturing method is provided in the experimental section, infra. Briefly, to prepare the subject microbial blend compositions, the microbes to be included in the composition are first identified. This identification step may include using microbes that are known to meet the above listed criteria or screening candidate microbes to determine whether they possess the desired criteria. Once the microbe constituents are identified, they are then matured or grown in culture, preferably separately and on a complex substrate, as described above. The separate grown and matured microbial cultures are then combined to produce the final microbial blend compositions, which may then be combined with a carrier, as desired.

The following examples are offered by way of illustration and not by way of limitation.

Experimental

I. Identification of Microbes

The beneficial, antagonistic strains are isolated from California farm land. They are natural, non-engineered isolates. Candidate isolates are put through a rigorous testing scheme before being considered for use in the finished suspension for commercial use:

A. Pathogen Antagonistic Assay:

1. Overview

Candidate agents are tested on "Challenge Plates" on which the petri dish-containing media is inoculated with 2 discs of one of 12 common soil-inhabiting pathogenic species—

(1) *Verticillium dahliae* (7) *Monilochaetes infuscans*

(2) *Fusarium solani* (8) *Rhizoctonia solani*

(3) *Cylindrocarpon obtusisporum* (9) *Sclerotinia sclerotiorum*

(4) *Pythium aphanidermatum* (10) *Sclerotinia minor*

(5) *Phytophthora megasperma* (11) *Sclerotium rolfsii*

(6) *Phymatotrichum omnivorum* (12) *Botrytis cinerea*

In this assay, a candidate beneficial antagonist must show aggressiveness against all 12 pathogenic species. A single streak of the candidate beneficial microbe is cultured between the 2 discs of the pathogen. The zone of inhibition to inward progressive growth of the pathogen manifests, in part, the potential antagonistic capabilities of the candidate.

2. Details

Method of Culturing Microbe Species Candidates:

a) Bacterial candidates are cultured on nutrient agar (Bacto Nutrient Agar, DIFCO Laboratories, Detroit, Mich.) as a standard agar medium (31 grams per liter of media)

b) Fungal candidates are cultured on potato dextrose agar (DIFCO Laboratories, Detroit, Mich.) as a standard agar medium (39 grams per liter of media)

c) Actinomycete candidates are cultured onto the following agar medium:

| Ingredient | Amount/Liter |
|---|---|
| Beef extract | 1 gr |
| Yeast extract | 1 gr |
| Tryptose | 2 gr |
| Glucose | 10 gr |
| Ferrous sulfate | trace |
| Agar | 15 gr |
| Water | 1,000 ml |

d) Candidate isolates are cultured onto appropriate media @ 25 deg C. Fungal species that require light for sporulation are cultured in the light. Otherwise, all other cultures are incubated in the dark.

e) Thriving cultures of the pathogen are also cultured on appropriate media. A 5 mm diameter disc is removed from the test agar plate and replaced with a matching disc from the pathogen culture. At the same time a 5 mm wide strip of candidate antagonist is streaked in the middle of the plate, exactly between the 2 pathogen discs. These will be referred to as "Challenge Plates". Two matching control plates are also set up at the same time: (a) With pathogen discs only and (b) With antagonist streak only.

f) The challenge and control plates are incubated in the dark at 25 deg C. and examined at 24 hour intervals.

g) Criteria for accepting a viable antagonist candidate are as follows:

(1) The antagonist must either match or exceed the rate of growth of the pathogen (2) If "zones of inhibition" are manifested, the zone of inhibition must exceed 25% impedance of the growth indicated on the pathogen control plate (3) Concomitantly, the growth of the antagonist must not be impeded by more than 25% of the growth observed on the antagonist candidate control plate (4) Antagonism must be observed within 48 hours (5) More than 50% of the pathogen growth must be impeded by the candidate antagonist B. Identification of Candidates and Evaluation of Plant/Animal Toxicity:

1. Overview

Candidates that pass the pathogen antagonism test are then identified to the species level, using any convenient protocol. Part of the reason for speciation is to clearly identify any possible animal or plant pathogens. Species that might be suspected of being potential animal or plant pathogens are tested as follows— a. Plant Pathogen Screening: Test Plants—Tomato Seedlings, Pepper Seedlings, Cucumber Seedlings, Radish Seedling, Grapevine Seedling.

Tests: Suspension Hypodermic Needle Injection Into Vascular Tissue

Suspension Spray+Humid Incubation b. Animal Pathogen Screening; Test Animals Rabbit & Mice Tests: Suspension Hypodermic Needle Subcutaneous Injection Suspension Spray Exposure/Lung Inhalation 2. Details Method of Pathogen Antagonism Screening with Indicator Plants—

Pots with various types of soil are prepared:

a) Sterilized control b) Inoculated with appropriate disease-causing levels of pathogens—

| Pathogen | Approx Inoculum per Gram Soil |
|---|---|
| *Verticillium dahliae* | 200+ cfu |
| *Fusarium solani* | 400+ cfu |
| *Rhizoctonia solani* | 30+ cfu |
| *Pythium aphanidermatum* | 300+ cfu |
| *Phytophthora megasperma* | 50+ cfu |
| *Phymatotrichum omnivorum* | 100+ cfu |
| *Monilochaetes infuscans* | 400+ cfu |
| *Sclerotinia sclerotiorum* | 5+ cfu |
| *S. minor* | 25+ cfu |
| *Sclerotium rolfsii* | 10+ cfu |
| *Botrytis cinerea* | 400+ cfu |

Forty eight hours after pathogen introduction, contaminated and control soils (250 cc) are drenched with a suspension of the candidate antagonist:

c) Bacteria are drenched at 50 ml of suspension @ approximately 1×10 ($12^{th}$) cfu per ml+5 ml liquid substrate (Pending USA patent application no. 9/222,459, the disclosure of which is herein incorporated by reference)

d) Fungi are drenched at 50 ml of suspension @ approximately 1×10 ($9^{th}$) cfu per ml+5 ml of liquid substrate (above)

e) Actinomycetes are drenched at 50 ml of suspension @ approximately 1×10 ($10^{th}$) per ml+5 ml of liquid substrate (above)

f) A control series is run with just 5 ml/250 cc soil of substrate alone

The pathogen+antagonist and control pots are allowed to incubate for 2 weeks, keeping the soil reasonably moist (~80% field capacity) throughout the 2 weeks, which allows for microbe activity.

At the end of 2 week's incubation, the pots are seeded with appropriate indicator plants.

Criteria utilized for the various pathogens are:

| Pathogen | Criteria for Antagonism | Passing Grade |
|---|---|---|
| *Verticillium dahliae* | Vascular wilt @ or after bloom | <10% of CK |
| *Fusarium solani* | Root & stem rot development | <10% of CK |
| *Cylindrocarpon obtusisporum* | Vascular wilt @ or after bloom | <10% of CK |
| *Pythium aphanidermatum* | Germination & stand % | >90% of CK |
| *Phytophthora megasperma* | Germination & stand % | >90% of CK |
| *Phymatotrichum omnivorum* | Germination & stand % | >90% of CK |
| *Monilochaetes infuscans* | Reisolation and titer of the pathogen | <10% of CK |
| *Rhizoctonia solani* | Root & stem rot; germ & stand % | <10% of CK |
| *Sclerotinia sclerotiorum* | Reisolation of sclerotia and viability | <10% of CK |
| *S. minor* | As for *S. sclerotiorum* | <10% of CK |
| *Sclerotium rolfsii* | Reisolation of sclerotia and viability | <10% of CK |
| *Botrytis cinerea* | Reisolation and titer of pathogen | <10% of CK |

Candidate antagonists which pass the plate and greenhouse bioassay are cultured onto appropriate agar plates and incubated @ 25 deg C. for 48–96 hours.

Rabbits and mice are exposed as follows:

a) Lung exposure—a liquid suspension of ~1×10 (6') cfu/ml is sprayed via an aerosol mist while the animal is placed within an air-tight enclosure. The same exposure is made to control animals but with sterile distilled water (CK).

b) Intravenous injection—a liquid suspension of ~1×10 ($6^{th}$) cfu/ml is injected behind the neck (~100 mcl). A control exposure utilizes 100 mcl of sterile distilled water.

c) Oral ingestion—a liquid suspension of ~1×10 ($6^{th}$) cfu/ml is sprayed onto food and drinking water replaced with 10 ml/100 ml water suspension. The control treatment merely covers the use of sterile distilled water sprayed over solid food.

For the lung and intravenous exposures, animals are allowed to resume their normal activities and observed for 2 months. Oral ingestion is allowed to continue for 1 week before normal activities are resumed and observed for 2 months. Criteria for evaluations are as follows:

d) Coughing or respiratory difficulties e) Lesions or infections f) Loss of weight or appetite g) Mortality All tests have a 0% tolerance for a discrepancy in any of the above categories C. Additional Screening Assays:

1. Overview

Candidate, beneficial microbes are further characterized based on alternative characteristics— a) Maximum temperature tolerance (preferably tolerant to at least 140 deg F.); this tends to select spore-forming bacteria, actinomycetes and resting stage spore-forming fungi b) Tolerant of pH range from 3.0–8.0 c) Rapid growth rate (when a central, circular inoculum is placed on media, the candidate must meet or exceed 1 cm beyond the circle edge within 24 hrs)

d) Retention of viability following a minimum of 120 days in liquid suspension @ 70 deg F.

2. Details

| Test | Method & Evaluation Criteria |
|---|---|
| a. Max Temp | Candidate antagonist cultured onto appropriate agar media<br>96 hr cultures exposed to: 140 deg F. for 96 hours<br>Reisolation and % viability determined<br>A 90%+ recovery is required to pass this test |
| b. pH Tolerance | Candidate antagonist suspensions set @ pH 3, 5 & 8 (1 × 10–$12^{th}$)<br>Exposed for 96 hours @ 25 deg C.<br>Reisolation and examination of titer<br>A 90%+ recovery is required to pass this test |
| c. Growth Rate | 5 mm discs of candidates are placed onto appropriate media (1 disc in the middle and 1 disc within each quadrant)<br>All are incubated at 25 deg C. in the dark except for species that require light (e.g. *Trichoderma* spp.)<br>Organisms must meet the following criteria:<br>a) Fungi - Fill the plate in 72 hours<br>b) Bact - Fill 60% of the plate within 96 hours<br>c) Act - Fill 60% of the plate within 96 hours |
| d. Viability | Candidates are grown and matured on appropriate agar media @ 25 deg C. for 120 hours.<br>Organisms are washed from the plates with a light saline solution (Ringer's Solution) and made up to 1 × 10 ($12^{th}$) concentration.<br>The containers are labeled and placed in dark rooms set @ 25 deg C. for 120 days<br>After exposure, the titer of viable organisms is tested<br>80%+ viability is required to pass the test |

D. Growth Enhancement Assays:

The safe and efficacious, beneficial, pathogen antagonistic microbes identified in the above assays are then further tested under simulated field conditions utilizing model, potted plant studies—

| | |
|---|---|
| e) Tomato Seedlings | + (1) *Pythium aphanidermatum*<br>+ (2) *Rhizoctonia solani*<br>+ (3) *Verticillium dahliae*<br>+ (4) *Fusarium oxysporum* |
| f) Lettuce Seedlings | + (1) *Pythium aphanidermatum*<br>+ (2) *Sclerotinia sclerotiorum* |
| c) Pepper Seedlings | + (1) *Phytophthora parasitica*<br>+ (2) *Rhizoctonia solani*<br>+ (3) *Sclerotium rolfsii*<br>+ (4) *Fusarium solani* |

g) Parameters Examined i. Germination and stand % ii. Completion of stand to production and/or harvest iii. Production and quality iv. Post-germination and post-stand infections II. Microbial Blend Preparation:

The beneficial, pathogenic antagonistic microbial candidates passing all tests described above are then mass produced individually in pure culture, allowed to mature, then blended together for the final product suspension. The following aqueous medium is employed for culture:

| Material | Targeted Ingredients | Rate/100 Gal Mix |
|---|---|---|
| Molasses | simple & complex sugars, cofactors, proteins | 2 gal |
| Ca Lignosulfonate | phenolic derivatives, various acids, complex sugars | 2 qt |
| Amino Acids | aliphatic, acidic, basic and other amino acids | 1 gal |
| Gallic Acid | phenolic acid | 1 lb |
| Yeast Extract | cofactors, vitamins | 10 lb |
| Tap Water | — | ~96 gal |

Note:

(1) The blend is ozonated for 6–12 hours to remove contaminants, then allowed to dissipate residual ozone for 2 hours with sterile air bubbling before a gallon of 48-hour liquid starter culture is added.

(2) The large inoculum of starter culture is farther assurance to avoid contamination.

(3) The culture is allowed to reach maturity for 72–120 hours following inoculation.

(4) Maturity is gauged by the final pH of the suspension. Most cultures are mature when the pH drops close to 4.0–4.5

(5) Cultures are then blended in equal volumes and homogenized in a stainless steel mixing vat.

(6) The natural, organic acid by-products induced to production assist in maintaining a quiescent state of the microbes.

(7) The mixed and defined suspension is containerized and stored between 36–70 deg F.

Note:

[1] Certain species of fungi (e.g. Trichoderma viride, Gliocladium virens) are cultured on cooked grain.

[2] The grain is first boiled in the media described above, then sterilized in an autoclave (120 psi, 240 deg F.)

[3] The sterilized, media-impregnated grain is then cooled and inoculated with pure spore suspensions of the required fungus, covered to prevent contamination and incubated between 70–80 deg F. for 1 week.

[4] Spores are harvested by submersing the grain culture (covered with spores) in Ringer's Salt Solution into which silicone surfactant is added to make a 100–200 ppm surfactant solution.

[5] The spore suspension is standardized to 1–10 billion per ml and the suspension added to the mixing vat in step 5 above (10 gal/100 gal mix).

III. Representative Specific Compositions and Methods of Use

A. Specific Formulations

| Material | Constitution | Volume/Gal | Final Product Appox Titer |
|---|---|---|---|
| Iota | *Bacillus subtilis* 201 | 16 oz | ~5 × 10 (11th) |
| | *Bacillus subtilis* 202 | 16 oz | ~5 × 10 (11th) |
| | *Comomonas acidovorans* | 16 oz | ~5 × 10 (11th) |
| | *Curtobacterium* sp. | 16 oz | ~5 × 10 (11th) |
| | *Pseudomonas fluorescens* 301 | 16 oz | ~5 × 10 (11th) |
| | *Bacillus thuringiensis* 102 | 16 oz | ~5 × 10 (11th) |
| | *Trichoderma viride* 401 | 32 oz | ~5 × 10 (9th) |
| Iota(+) | *B. subtilis* 201 | 16 oz | ~5 × 10 (11th) |
| | *B. subtilis* 202 | 16 oz | ~5 × 10 (11th) |
| | *B. thuringiensis* 101 | 21 oz | ~7 × 10 (11th) |
| | *B. thuringiensis* 102 | 21 oz | ~7 × 10 (11th) |
| | *B. thuringiensis* 103 | 21 oz | ~7 × 10 (11th) |
| | *Trichoderma viride* 401 | 32 oz | ~5 × 10 (9th) |
| Asunder | Heat inactivated corn seed | 50 lbs | ~2 × 10 (11th) |
| | Iota (+) suspension | 250 ml | |
| | Spreader Sticker | 2 ml | |

B. Benefits

| Product | Benefits | Measure of Benefit |
|---|---|---|
| Soil: Iota | 1) Antagonism of soil-borne pathogens | 1) 10%–100% reduction in inoculum levels |
| | 2) Antagonism of soil-overwintering pathogens | 2) 10%–100% reduction |
| | 3) Increased release of tied-up materials | 3) 25%–500% increase |
| | 4) Antagonism of pests and nematodes | 4) 10%–100% reduction |
| | 5) Increaded water infiltration rates | 5) 25%–800% increase |
| | 6) Increased water-holding capacity of soil | 6) 5%–50% increase |

-continued

| Product | Benefits | Measure of Benefit |
|---|---|---|
| Iota Foliar: | 1) Aerial pathogen antagonism | 1) 10–100% reduction |
| | 2) Aerial pest antagonism | 2) 10–100% reduction |
| | 3) Reduced freeze hypersensitivity | 3) 10–100% reduction |
| | 4) Extended shelf life of fruits & vegetables | 4) 10–100% increase |
| Asunder: | 1) Antagonism of insect pests | 1) 10–100% reduction |
| | 2) Antagonism of soil-borne pathogens | 2) 10–100% reduction |
| | 3) Antagonism of soil-overwintering pathogens | 3) 10–100% reduction |
| | 4) Increased release of tied-up minerals | 4) 10–100% increase |
| | 5) Antagonism of nematode pests | 5) 10–100% reduction |

C. Additional Formulation

| Ingredient | Amount per Lb. |
|---|---|
| Heat-Inactivated Corn Seed | |
| *Bacillus thuringiensis* 101 | 1.2 ml |
| *Bacillus thuringiensis* 102 | 1.2 ml |
| *Bacillus thuringiensis* 103 | 1.2 ml |
| *Bacillus subtililis* 201 | 1.2 ml |

Note: Each liquid culture of microorganisms contains 1×10 ($9^{th}$)–1×10 ($14^{th}$) cfu/ml IV. Characterization Assays:

A. *Rhizoctonia solani* suppression—

Sandy loam soil in 6" diameter clay pots sterilized by autoclaving (120 psi, 110 deg C., 1 hr)

Pathogen treatments—

Inoculated with 10 sclerotia per gram of soil (Control)

Inoculated with 10 sclerotia per gram of soil (Treatment)

Antagonist treatments (per 250 cc soil)—

Drenched with 50 ml sterile water (Control)

Drenched with 50 ml of Iota suspension (1×10 ($12^{th}$ cfu/ml)+5 ml liquid substrate U.S. patent application no. 9/222,459, the disclosure of which is herein incorporated by reference)

Allowed to incubate 14 days:

25 deg C.

80% field capacity wetness

~16 hours light+8 hours darkness

After 14 days incubation, 10 control and 10 treatment pots planted with green bean (*Phaseolus vulgaris*)

After 21 days, inspected for root and stem lesions and rated on a 1–10 scale with 10 representing maximum disease

*Rhizoctonia solani*: Antagonism in the Soil with Iota

| Treatment | 1 | 2 | 3 | 4 | 5 | 6 | 7 | 8 | 9 | 10 | Total | Mean |
|---|---|---|---|---|---|---|---|---|---|---|---|---|
| Control | 9 | 8 | 10 | 9 | 9 | 7 | 10 | 8 | 9 | 9 | 88 | 8.8 a |
| Iota | 1 | 2 | 1 | 1 | 1 | 1 | 1 | 2 | 1 | 1 | 12 | 1.2 b |

B. *Verticillium dahliae* suppression—

1. Sandy loam soil in 6" diameter clay pots sterilized as for *R. solani*
2. Pathogen treatments —
   a) Inoculated with 200 microsclerotia per gram of soil (Control)
   b) Inoculated with 200 microsclerotia per gram of soil (Treatment)
3. Antagonist treatments (per 250 cc soil)—
   a) Drenched with 50 ml sterile water (Control)
   Drenched with 50 ml of Iota suspension (1×10 ($12^{th}$) cfu/ml)+5 ml liquid substrate (U.S. patent application no. 9/222,459, the disclosure of which is herein incorporated by reference)
   b) Allow to incubate 21 days:
   (1) 25 deg C.
   (2) 80% field capacity wetness
   (3) ~16 hours light+8 hours darkness
4. After 21 days incubation, 10 control and 10 treatment pots planted with green bean (*Phaseolus vulgaris*)
5. Plants allowed to grow past bloom and into fruit set before evaluation of disease. Plants were evaluated for visible wilt symptoms and given a 1–10 rating with 10 representing maximum disease.

*Verticillium dahliae*: Antagonism in the Soil with Iota

| Treatment | 1 | 2 | 3 | 4 | 5 | 6 | 7 | 8 | 9 | 10 | Total | Mean |
|---|---|---|---|---|---|---|---|---|---|---|---|---|
| Control | 10 | 10 | 9 | 10 | 10 | 10 | 9 | 10 | 9 | 10 | 97 | 9.7 a |
| Iota | 1 | 1 | 1 | 1 | 1 | 1 | 1 | 1 | 1 | 1 | 10 | 1.0 b |

C. *Sclerotium rolfsii* suppression—

Identical soil preparation as per *R. solani*

Pathogen treatments same as per *R. solani* but with *S. rolfsii*

Antagonist treatment same as per *R. solani* but incubation time increased to 21 days After 21 days incubation, 10 control and 10 treatment pots planted with green bean (*Phaseolus vulgaris*)

Plants allowed to grow 10 days past fruit set before evaluation for crown rot. Rated on a l-10 scale with 10 representing maximum disease.

*Sclerotium rolfsii*: Antagonism in the Soil with Iota

| Treatment | 1 | 2 | 3 | 4 | 5 | 6 | 7 | 8 | 9 | 10 | Total | Mean |
|---|---|---|---|---|---|---|---|---|---|---|---|---|
| Control | 10 | 10 | 10 | 10 | 10 | 9 | 10 | 10 | 10 | 10 | 99 | 9.9 a |
| Iota | 1 | 1 | 1 | 1 | 1 | 1 | 1 | 1 | 1 | 1 | 10 | 1.0 b |

D. Phytophthora cactorum suppression—

Soil prepared as per *R. solani*

Pathogen treatments —
   Inoculated with 40 cfu per ml (Control)
   Inoculated with 40 cfu per ml (Treatment)

Antagonist treatments (per 250 cc soil)—
   Drenched with sterile water
   Drenched with 50 ml Iota suspension (1×10 ($12^{th}$) cfu/ml)+5 ml liquid substrate (U.S. patent application no. 9/222,459, the disclosure of which is herein incorporated by reference)
   Allowed to incubate 14 days:
   25 deg C.
   80% field capacity wetness
   ~16 hours light+8 hours darkness After 14 das incubation, 10 control and 10 treatment pots planted with green bean (*Phaseolus vulgaris*)

Plants allowed to grow for 21 days before evaluation for crown and rot rot. Rated on a 1–10 scale with 10 representing maximum disease.

*Phytophthora cactorum*: Antagonism in the Soil with Iota

| Treatment | 1 | 2 | 3 | 4 | 5 | 6 | 7 | 8 | 9 | 10 | Total | Mean |
|---|---|---|---|---|---|---|---|---|---|---|---|---|
| Control | 10 | 10 | 10 | 10 | 10 | 10 | 10 | 10 | 10 | 10 | 100 | 10 a |
| Iota | 2 | 2 | 2 | 1 | 4 | 2 | 3 | 1 | 2 | 2 | 21 | 2.1 b |

E. *Botrytis cinerea* suppression—

Soils prepared as per *R. solani*

Pathogen treatments—
   Inoculated with -400 cfu per gram of soil (Control)
   Inoculated with -400 cfu per gram of soil (Treatment)

Antagonist treatments (per 250 cc soil)—
   Drenched with 50 ml sterile water (Control)
   Drenched with 50 ml of Iota suspension (1×10 ($12^{th}$) cfu/ml)+5 ml liquid substrate (U.S. patent application no. 9/222,459, the disclosure of which is herein incorporated by reference)
   Allowed to incubate 14 days:
   25 deg C.
   80% field capacity wetness
   ~16 hours light+8 hours darkness After 14 days incubation, 10 control and 10 treatment pots isolated for *Botrytis cinerea* inoculum levels Evaluation based on cfu's recovered based on a 400 cfu/ml inoculation. Rating was based on a 1–10 scale with 10 representing maximum recovery of the pathogen.

*Botrytis cinerea*: Antagonism in the Soil with Iota

| Treatment | 1 | 2 | 3 | 4 | 5 | 6 | 7 | 8 | 9 | 10 | Total | Mean |
|---|---|---|---|---|---|---|---|---|---|---|---|---|
| Control | 10 | 10 | 10 | 10 | 10 | 10 | 10 | 10 | 10 | 10 | 100 | 10 a |
| Iota | 3 | 2 | 2 | 1 | 1 | 3 | 3 | 2 | 3 | 3 | 23 | 2.3 b |

F. *Sclerotinia scierotiorum* suppression—

Soil preparation as per *R. solani*

Pathogen treatments—

Inoculated with 5 sclerotia per gram of soil and placed in nylon sock and buried in the potting soil (Control)

Inoculated with 5 sclerotia per gram of soil as above (Treatment)

Antagonist treatments (per 250 cc soil)—

Drenched with 50 ml sterile water (Control)

Drenched with 50 ml of Iota suspension (1×10 (12th) cfu/ml)+5 ml liquid substrate (U.S. patent application no. 9/222,459, the disclosure of which is herein incorporated by reference)

Allowed to incubate 21 days:

25 deg C.

80% field capacity wetness

~16 hours light+8 hours darkness

After 21 days incubation, 10 control and 10 treatment pots examined for sclerotia viability.

Viability based on a 1–10 rating with 10 representing maximum viability

*Sclerotinia sclerotiorum*: Antagonism in the Soil with Iota

| Treatment | 1 | 2 | 3 | 4 | 5 | 6 | 7 | 8 | 9 | 10 | Total | Mean |
|---|---|---|---|---|---|---|---|---|---|---|---|---|
| Control | 10 | 10 | 10 | 10 | 10 | 10 | 10 | 10 | 10 | 10 | 100 | 10 a |
| Iota | 1 | 1 | 1 | 1 | 1 | 1 | 1 | 1 | 1 | 1 | 10 | 1 b |

The above discussion and results demonstrate that the subject microbial blend compositions provide for significant benefits in the field of agriculture, where use of the subject compositions in accordance with the subject methods provides for significantly improved results. As such, the subject invention represents a significant contribution to the art.

All publications and patent applications mentioned in this specification are herein incorporated by reference to the same extent as if each individual publication or patent application was specifically and individually indicated to be incorporated by reference.

The invention now being fully described, it will be apparent to one of skill in the art that many changes and modifications can be made thereto without departing from the spirit and scope of the appended claims.

What is claimed is:

1. A composition comprising:

(a) a plurality or distinct microbial species made up of at least 5 different bacterial species and at least 2 different fungal species, wherein each constituent member of said plurality is:

(i) antagonistic against a plurality of microbial pathogens;

(ii) non-pathogenic towards plants and animals;

(iii) tolerant of high temperatures;

(iv) grows rapidly; and (v) has been proliferated on a complex substrate; and (b) a carrier.

2. The composition according to claim 1, wherein said carrier is a liquid.

3. The composition according to claim 1, wherein said carrier is a solid.

4. A composition comprising a carrier a plurality of distinct microbial species wherein each constituent of said plurality is:

(a) antagonistic against a plurality of microbial pathogens;

(b) non-pathogenic towards plants and animals;

(c) tolerant of high temperatures;

(d) grows rapidly; and (e) proliferates on a complex substrate, wherein said plurality is made up of at least 5 different bacterial species and at least 2 different fungal species and comprises Bacillus subtilis and at least one of: *Bacillus thuringiensis, Curtobacterium* sp., *Arthrobacter paraffineus, Pseudomonas fluorescens* and *Comomonas acidovorans*, wherein each member of said plurality has been proliferated on a complex substrate.

5. The composition according to claim 4, wherein said plurality comprises at least 5 distinct microbial species.

6. The composition according to claim 5, wherein said plurality comprises at least 5 bacterial species.

7. The composition according to claim 5, wherein said plurality comprises at least 2 fungal species.

8. The composition according to claim 4, wherein said composition comprises a carrier.

9. The composition according to claim 8, wherein said carrier is a liquid.

10. The composition according to claim 8, wherein said carrier is a solid.

11. In an agricultural method, the improvement comprising:

applying to at least one of soil or plant tissue a composition according to claim 4.

12. A method of producing a composition according to claim 4, said method comprising:

(a) identifying a plurality of microbial species comprising Bacillus subtilis and at least one of: *Bacillus thuringiensis, Curtobacterium* sp., *Arthrobacter*

*paraffineus, Pseudomonas fluorescens* and *Comomonas acidovorans*, wherein each member of said plurality is:

(i) antagonistic against a plurality or microbial pathogens;

(ii) non-pathogenic towards plants and animals;

(iii) tolerant of high temperatures;

(iv) grows rapidly; and (v) proliferates on a complex substrate;

(b) proliferating said plurality on a complex substrate, and (c) combining said plurality to produce said composition.

13. The method according to claim 12, wherein said method further comprises separately proliferating each species prior to said combining.

14. The method according to claim 13, wherein said method further comprises combining said composition with a carrier.

15. The method according to claim 14, wherein said carrier is a fluid.

16. The method according to claim 14, wherein said carrier is a solid.

17. The method according to claim 12, wherein said identifying comprises subjecting a candidate microbial species to a series of assays which identify whether the species has all of said (i)–(v) characteristics.

* * * * *